United States Patent [19]

Tracy

[11] 4,278,821
[45] Jul. 14, 1981

[54] ω,ω-BIS(DIALKYLHYDROXYPHENYL) ALKANOLS AS INTERMEDIATES IN MAKING EFFECTIVE ANTIOXIDANTS

[75] Inventor: David J. Tracy, Lincoln Park, N.J.

[73] Assignee: GAF Corporation, New York, N.Y.

[21] Appl. No.: 62,762

[22] Filed: Aug. 1, 1979

[51] Int. Cl.³ .............................................. C07C 39/12
[52] U.S. Cl. .............................. 568/723; 260/45.85 B; 260/45.95 F; 260/410.5; 568/727
[58] Field of Search ................................ 568/723, 727

[56] References Cited

U.S. PATENT DOCUMENTS

| 3,057,928 | 10/1962 | Koblitz et al. | 568/718 |
| 3,103,501 | 9/1963 | Shearer et al. | 260/45.95 |

FOREIGN PATENT DOCUMENTS 46-01251  1/1971  Japan ........................ 568/723

Primary Examiner—Robert Gerstl
Attorney, Agent, or Firm—James Magee, Jr.; Walter Katz

[57] ABSTRACT

This invention describes novel intermediate alkanols for making effective compounds, which intermediates are ω,ω-bis(dialkylhydroxyphenyl) alkanols having the formula:

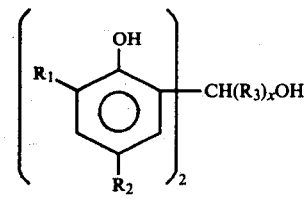

wherein
$R_1$ is a tertiary alkyl group having 4–8 carbon atoms;
$R_2$ is alkyl having 1–4 carbon atoms;
$R_3$ is a straight chain or branched alkylene group having 1–4 carbon atoms; and
x is 1–4.

6 Claims, No Drawings

ω,ω-BIS(DIALKYLHYDROXYPHENYL) ALKANOLS AS INTERMEDIATES IN MAKING EFFECTIVE ANTIOXIDANTS

BACKGROUND OF THE INVENTION

1. Field of the Invention

This invention relates to antioxidants, and more particularly, to new intermediate compounds, and their use for synthesizing novel stabilizing organic compounds which are effective against thermo-oxidative degradation.

2. Description of the Prior Art

It is known to employ derivatives of sterically hindered phenols as stabilizers for plastics against thermo-oxidative degradation or degradation induced by light. However, many of these compounds do not afford long life protection against these degradative effects, and others exhibit the disadvantage that they discolor the organic polymer in an objectionable manner either when they are incorporated or under the action of light or on contact with industrial flue gases or even on contact with hot water, which greatly limits their applicability in industry. Now new compounds have been found which, surprisingly, are outstandingly suitable for stabilizing organic polymers.

The prior art is represented by such U.S. patents as U.S. Pat. Nos. 3,057,928; 3,210,428; 3,275,597; 3,354,118; and 4,132,702; and Belgium Pat. No. 652,510.

3. Relates Copending Patent Applications (a) FDN-215, Ser. No. 062,761, filed Aug. 1, 1979, describes and claims novel antioxidant compounds, and organic material stabilized with their aid.

(b) FDN-215/B, Ser. No. 062,763, filed Aug. 1, 1979, describes and claims a method of making the said intermediate and antioxidant compounds.

SUMMARY OF THE INVENTION

This invention describes novel intermediate alkanols for making effective compounds, which alkanols are ω,ω-bis(dialkylhydroxyphenyl) alkanols having the formula:

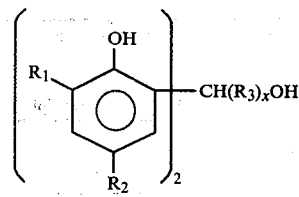

wherein
 $R_1$ is a tertiary alkyl group having 4–8 carbon atoms;
 $R_2$ is alkyl having 1–4 carbon atoms;
 $R_3$ is a straight chain or branched alkylene group having 1–4 carbon atoms; and,
 $x$ is 1–4.

DETAILED DESCRIPTION OF THE INVENTION

The antioxidant compounds are made by esterification of the corresponding alkanol intermediates with a suitable acid or derivative thereof. The alcohols are synthesized by condensation of a suitable substituted phenol with a hydroxyaldehyde or precurser thereof in the following manner.

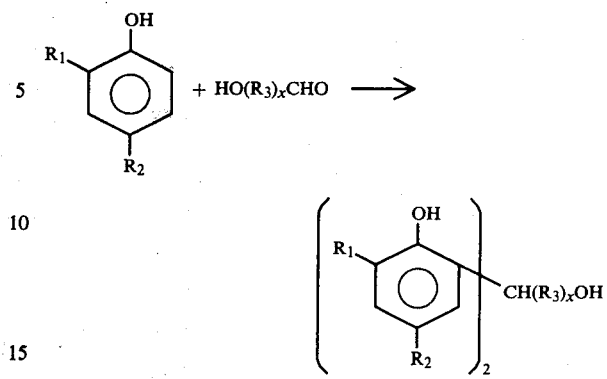

where $R_1$, $R_2$, $R_3$ and $x$ are as defined above.

Generally the phenol and hydroxyaldehyde starting materials are commercially available, or may be readily synthesized by known methods in preparative organic chemistry. Typical $R_1$ groups include tert. butyl and diisobutyl; $R_2$ is methyl, ethyl, propyl, butyl, and tert. butyl; $R_3$ is propylene; and $x$ is 1–4.

The hydroxyaldehyde starting material also may be made in situ from a suitable furan compound, for example, 2,3-dihydrofuran, which is made by 1,4-butenediol by dehydration and isomerization, as is known in the art. The furan compound, in acid solution, affords the desired γ-hydroxybutyldehyde starting material.

The condensation usually is carried out without solvent at a temperature of about 25° to 75° C., preferably about 55° C., for about ½–3 hours, preferably an hour. The excess phenolic reactant then is distilled off and the product crystallized.

EXAMPLE 1

Preparation of 4,4-di(2-hydroxy-3-t-butyl-5-methylphenyl) butanol

To
123.0 g. (0.75 mole) of 2-t-butyl-4-methylphenol and
75 g. of concentrated hydrochloric acid (37%) (under nitrogen was added over a 45 minute period at 53°–56°
17.5 g. (0.25 mole) 2,3-dihydrofuran. Approximately 15 minutes after addition was complete the reaction mixture solidified making stirring impossible. Ether was added to dissolve the solid and the reaction product washed with water and concentrated to 133 g. of residue. The excess 2-t-butyl-4-methylphenol was distilled off (40.0 g.) and the residue (75 g.) was crystallized three times from heptane, m.p. 132°–134°. The yield was 59.0 g. (59%). The infrared showed bands at 3610, 3480 and 860 cm-[1]. The NMR showed a singlet in the aromatic region.

Anal. Calcd. for $C_{26}H_{38}O_3$: C, 78.34; H, 9.60; MW, 398. Found: C, 77.61; H, 9.96; MW. 375.

EXAMPLE 2

Preparation of 5,5-di(2-hydroxy-3-t-butyl-5-methylphenyl) pentanol

To
246.0 g (1.5 mole) 2-t-butyl-p-cresol and
150.0 g of concentrated hydrochloric acid (37%) under nitrogen was added over a 30 minute period at 55°–60°

51.0 g (0.5 mole) of 5-hydroxypentanal. The temperature was maintained for 5 hours. The reaction mixture was diluted with ether washed with water, dried over sodium sulfate and concentrated to 225.0 g. Excess 2t-butyl-p-cresol was distilled off (72.1 g.) leaving 108.0 g. of residue. The oil had infrared bands at 3340 and 3500 cm$^{-1}$. It was transparent in the aldehyde region.

Anal.Calcd. for $C_{27}H_{40}O_3$: C, 78.59; H, 9.77. Found: C, 77.32; H, 9.23.

EXAMPLE 3

Preparation of 4,4-di(2-hydroxy-3-diisobutyl-5-methylphenyl) butanol

A. 2-Diisobutyl-4-methylphenol

To
- 216.0 g (2.0 mole) p-cresol (freshly distilled) was added
- 12.0 g of gaseous boron trifluoride (bubbled in). Heat to 52° C. and added slowly over 1 hour. 220 g (2.0 mole) diisobutylene. The reaction exothermed to 58° C. during addition. Hold reaction mixture at 55°-60° C. for 4 hours. Add:
- 80 ml water and separate the water layer, neutralize the oil layer with sodium hydroxide. The product was distilled yielding 88 g boiling between 100° and 170° at 0.5 to 1.0 mm of Hg. The infrared and nuclear magnetic resonance spectra agreed with the structure.

Anal. Calcd. for $C_{15}H_{24}O$: C, 81.92; H, 10.98. Found: C, 82.24; H. 10.82.

This compound was used as a starting material to prepare the alcohol of Example 8.

B.

To
- 165.0 g (0.75 mole) of 2-diisobutyl-4-methylphenol and
- 75.0 g of concentrated hydrochloric acid (37%) under nitrogen was added over a 45 minute period at 50-60° C.
- 17.5 g (0.25 mole) 2,3-dihydrofuran. Approximately 15 minutes after addition a solid mass formed. Ether was added and the product washed with water and concentrated. The excess phenol was removed by distillation. The residue was purified by crystallization from heptane. The off-white solid, formed in 60% yield, had an infrared and nuclear magnetic resonance in agreement with the structure.

EXAMPLE 4

Preparation of 2,2-di(2-hydroxy-3-t-butyl-5-methylphenyl) ethanol

To
- 246.0 g (1.5 mole) 2-t-butyl-p-cresol and
- 150.0 g concentrated hydrochloric acid (37%) under nitrogen was added over a 30 minute period at 55-60° C.
- 30.0 g (0.5 mole) glycoladehyde. The temperature was maintained for 6 hours. The reaction mixture was diluted with ether, washed with water, dried over sodium sulfate, and concentrated to 220.0 g. Excess 2-t-butyl-p-cresol was distilled off leaving 150 g. of residue. The material had hindered hydroxyl absorption at 3340 and 3500 cm$^{-1}$, and was transparent in the aldehyde region.

EXAMPLE 5

Preparation of 2,2-dimethyl-3,3-di(2-hydroxy-3-t-butyl-5-methylphenyl)propanol

To
- 246.0 g (1.5 mole) 2-t-butyl-p-cresol and
- 150.0 g concentrated hydrochloric acid (37%) under nitrogen was added over a 30 minute period at 55-60°.
- 51.0 g (0.5 mole) 2,2-dimethylhydracryladehyde. The temperature was maintained for 6 hours. After dilution with ether, the material was washed with water. The excess phenol was removed by distillation, leaving an off-white solid in 50% yield. The infrared and nuclear magnetic resonance agreed with the structure.

The unusual antioxidant effect of the esterified products of this invention in protecting polymers, e.g. polypropylene was illustrated in detail in the copending application, FDN-215. The alkanols, however, also are useful antioxidants relative to the polymer itself as shown below.

EXAMPLE 6

The antioxidant system was compounded into unstabilized polypropylene on a Banbury type laboratory mill (Brabender Plastograph) at 183° C. for 10 minutes. A 40 mil. thick sheet of compounded material was compression molded on a laboratory press (Carver) using 245° C. platen temperatues, 10,000 lbs. pressure on the 2¼ inch diameter ram, and a dwell time of 2 minutes. The sheets were air cooled under pressure before removal from the press. Standard microdumbell specimens (ASTM D 1708-59T) were die cut from the sheet. No discoloration was noted in the specimen. The specimens were suspended vertically in an air circulating oven operating at 300° F. Time to initial failure is noted as the exposure time required for first signs of microcracking or crazing of specimen. Time to final failure was noted as the exposure time required to produce breaking of the specimen when flicked with the finger.

| Effect of Intermediate Additive on Polypropylene | | |
|---|---|---|
| | Concentration(phr) | Hours to Failure |
| Polypropylene | | 2 |
| Alcohol of Example 1 | 0.5 | 58–82 |

What is claimed is:

1. A compound of the formula:

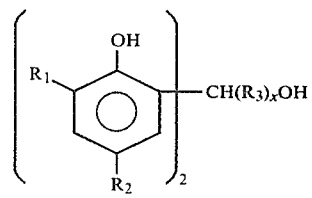

wherein
R$_1$ is a diisobutyl group;

R₂ is alkyl having 1-4 carbon atoms;
R₃ is a straight chain or branched alkylene group having 1-4 carbon atoms; and
x is 1-4.

2. A compound of the formula:

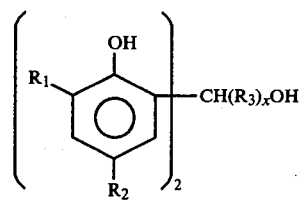

wherein
R₁ is a tertiary alkyl group having 4-8 carbon atoms;
R₂ is alkyl having 1-4 carbon atoms;
R₃ is propylene;
x is 1-4.

3. A compound of the formula:

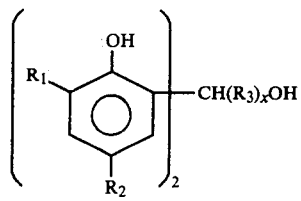

wherein
R₁ is a tertiary alkyl group having 4-8 carbon atoms;
R₂ is alkyl having 1-4 carbon atoms;
R₃ is a straight chain or branched alkylene group having 1-4 carbon atoms; and
x is 3.

4. 4,4-di(α-hydroxy-3-t-butyl-5-methylphenyl) butanol.

5. 4,4-di(2-hydroxy-3-diisobutyl-5-methylphenyl) butanol.

6. 2,2-di(2-hydroxy-3-t-butyl-5-methylphenyl) ethanol.

* * * * *